(12) United States Patent
Hur et al.

(10) Patent No.: US 10,987,670 B2
(45) Date of Patent: Apr. 27, 2021

(54) ELECTRODE ARRAY FOR VORTEX-ASSISTED ELECTROPORATION

(71) Applicant: President and Fellows of Harvard College, Cambridge, MA (US)

(72) Inventors: Soojung Claire Hur, Baltimore, MD (US); Mengxing Ouyang, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 670 days.

(21) Appl. No.: 15/566,551

(22) PCT Filed: Apr. 14, 2016

(86) PCT No.: PCT/US2016/027581
§ 371 (c)(1),
(2) Date: Oct. 13, 2017

(87) PCT Pub. No.: WO2016/168492
PCT Pub. Date: Oct. 20, 2016

(65) Prior Publication Data
US 2018/0117592 A1    May 3, 2018

Related U.S. Application Data

(60) Provisional application No. 62/147,492, filed on Apr. 14, 2015.

(51) Int. Cl.
*B01L 3/00* (2006.01)
*C12M 1/42* (2006.01)
(Continued)

(52) U.S. Cl.
CPC ....... *B01L 3/502761* (2013.01); *C12M 35/02* (2013.01); *C12N 1/06* (2013.01);
(Continued)

(58) Field of Classification Search
None
See application file for complete search history.

(56) References Cited

U.S. PATENT DOCUMENTS 4,231,938 A   11/1980  Monaghan et al.
6,074,605 A    6/2000  Meserol et al.
(Continued)

FOREIGN PATENT DOCUMENTS

CN        105593366       5/2016
WO      WO-97-32992 A1   9/1997
(Continued)

OTHER PUBLICATIONS

"U.S. Appl. No. 13/961,084, Non Final Office Action dated Aug. 20, 2014", 11 pgs.
(Continued)

*Primary Examiner* — William H. Beisner
(74) *Attorney, Agent, or Firm* — Schwegman Lundberg & Woessner, P.A.

(57) ABSTRACT

A device includes a microfluidic trap disposed along a microfluidic channel, the trap and channel having dimensions to create a fluid vortex within the trap to trap a particle of interest and an electrode having interdigitated electrically isolated fingers positioned in the trap to create an electric field across the trap such that the electric field causes electroporation of a molecule into the particle of interest. A further device includes an array of channels, traps and interdigitated electrically isolated fingers.

8 Claims, 7 Drawing Sheets

(51) Int. Cl.
*C12N 13/00* (2006.01)
*C12N 1/06* (2006.01)
*C12N 15/87* (2006.01)
*C12M 3/06* (2006.01)

(52) U.S. Cl.
CPC .......... *C12N 1/066* (2013.01); *C12N 13/00* (2013.01); *B01L 2200/0668* (2013.01); *B01L 2300/0877* (2013.01); *B01L 2400/0415* (2013.01); *B01L 2400/0463* (2013.01); *C12M 23/16* (2013.01); *C12N 15/87* (2013.01)

(56) References Cited

U.S. PATENT DOCUMENTS

| | | | |
|---|---|---|---|
| 7,473,361 | B2 | 1/2009 | Craighead |
| 9,029,109 | B2 | 5/2015 | Hur et al. |
| 2004/0180392 | A1 | 9/2004 | Prueksaritanont |
| 2005/0026283 | A1 | 2/2005 | Ormar et al. |
| 2005/0112544 | A1* | 5/2005 | Xu .......... G01N 27/02 435/4 |
| 2005/0164161 | A1* | 7/2005 | Augustine ........ G01N 33/5008 435/4 |
| 2009/0326436 | A1 | 12/2009 | Rubinsky et al. |
| 2010/0159439 | A1 | 6/2010 | Orwar et al. |
| 2011/0027235 | A1 | 2/2011 | Gregory et al. |
| 2011/0104128 | A1 | 5/2011 | Cooper et al. |
| 2011/0189650 | A1 | 8/2011 | Ayliffe et al. |
| 2012/0004144 | A1 | 1/2012 | Perroud et al. |
| 2012/0219987 | A1* | 8/2012 | Mussivand .......... C12N 1/066 435/40.5 |
| 2013/0171628 | A1 | 7/2013 | Di Carlo et al. |
| 2015/0044750 | A1 | 2/2015 | Hur et al. |
| 2015/0232800 | A1 | 8/2015 | Hur et al. |
| 2017/0183644 | A1 | 6/2017 | Vickers et al. |
| 2018/0340186 | A1 | 11/2018 | Hur |

FOREIGN PATENT DOCUMENTS

| | | |
|---|---|---|
| WO | WO-03-023020 A1 | 3/2003 |
| WO | 2011142813 | 11/2011 |
| WO | 2012037030 | 3/2012 |
| WO | WO-2014-172340 A1 | 10/2014 |
| WO | 2015021270 | 2/2015 |
| WO | 2016011059 | 1/2016 |
| WO | WO-2016168492 A1 | 10/2016 |
| WO | WO-2017-066624 A1 | 4/2017 |

OTHER PUBLICATIONS

"U.S. Appl. No. 13/961,084, Response filed Nov. 5, 2014 to Non Final Office Action dated Aug. 20, 2014", 8 pgs.
"U.S. Appl. No. 13/961,084, Examiner Interview Summary dated Oct. 30, 2014", 3 pgs.
"U.S. Appl. No. 13/961,084, Examiner Interview Summary dated Nov. 12, 2014", 3 pgs.
"U.S. Appl. No. 13/961,084, Notice of Allowance dated Nov. 18, 2014", 5 pgs.
"International Application Serial No. PCT/US2014/050137, Invitation to Pay Additional Fees and Partial Search Report dated Nov. 20, 2014", 3 pgs.
"U.S. Appl. No. 13/961,084, Notice of Allowance dated Jan. 14, 2015", 8 pgs.
"International Application Serial No. PCT/US2014/050137, International Search Report dated Jan. 23, 2015", 4 pgs.
"International Application Serial No. PCT/US2014/050137, Written Opinion dated Jan. 23, 2015", 5 pgs.
"U.S. Appl. No. 14/703,648, Preliminary Amendment filed May 5, 2015", 7 pgs.
"International Application Serial No. PCT/US2015/040422, International Search Report dated Oct. 19, 2015", 4 pgs.
"International Application Serial No. PCT/US2015/040422, Written Opinion dated Oct. 19, 2015", 6 pgs.
"International Application Serial No. PCT/US2014/050137, International Preliminary Report on Patentability dated Feb. 18, 2016", 7 pgs.
"U.S. Appl. No. 14/703,648, Restriction Requirement dated Jun. 27, 2016", 7 pgs.
"U.S. Appl. No. 14/703,648, Response filed Jul. 28, 2016 to Restriction Requirement dated Jun. 27, 2016", 3 pgs.
"U.S. Appl. No. 14/703,648, Non Final Office Action dated Oct. 7, 2016", 23 pgs.
"U.S. Appl. No. 14/703,648, Response filed Jan. 9, 2017 to Non Final Office Action dated Oct. 7, 2016", 10 pgs.
"International Application Serial No. PCT/US2015/040422, International Preliminary Report on Patentability dated Jan. 26, 2017", 8 pgs.
"European Patent Application Serial No. 14834768.5, Supplementary European Search Report dated Feb. 7, 2017", 5 pgs.
"U.S. Appl. No. 14/703,648, Final Office Action dated Mar. 17, 2017", ', 18 pgs.
"European Application Serial No. 14834768.5, Extended European Search Report dated May 12, 2017", 8 pgs.
"U.S. Appl. No. 14/703,648, Response filed May 17, 2017 to Final Office Action dated Mar. 17, 2017", 9 pgs.
"U.S. Appl. No. 14/703,648, Advisory Action dated May 26, 2017", 3 pgs.
"U.S. Appl. No. 15/406,210, Restriction Requirement dated Jun. 6, 2017", 6 pgs.
"U.S. Appl. No. 14/703,648, Response filed Jun. 7, 2017 to Advisory Action dated May 26, 2017", 10 pgs.
"U.S. Appl. No. 14/703,648, Advisory Action dated Jun. 16, 2017", 3 pgs.
"U.S. Appl. No. 15/406,210, Response filed Aug. 7, 2017 to Restriction Requirement dated Jun. 6, 2017", 7 pgs.
"U.S. Appl. No. 15/406,210, Non Final Office Action dated Nov. 14, 2017", 17 pgs.
Al-Lazikani, "Combinatorial drug therapy for cancer in the post-genomic era", Nature Biotechnology, vol. 30, No. 7, (Jul. 10, 2012), 1-13.
Geng, "Transfection of cells using flow-through electroporation based on constant voltage", Nature Protocols, vol. 6, No. 8, (Jul. 21, 2011), 1192-1208.
Geng, Tao, "Transfection of cells using flow-through electroporation based on constant voltage", Nature America, Inc. vol. 6 No. 8, (Jul. 21, 2011), 1192-1208.
Herling, T.W., "Integration and characterization of solid wall electrodes in microfluidic devices fabricated in a single photolithography step", Department of Physiology, Development and Neuroscience,University of Cambridge, Downing Street, Cambridge CB2 3DY, United Kingdom (Dated: May 16, 2013), (May 16, 2013), 1-5.
Hur, "High-throughput size-based rare cell enrichment using microscale vortices", Biomicrofluidics, (2011).
Lieu, V H, "Hydrodynamic tweezers: Impact of design geometry on flow and microparticle trapping", Analytical Chemistry 84, (1963-1968), 2012.
Park, J S, "Continuous focusing of microparticles using inertial lift force and vorticity via multi-orifice microfluidic channels", (2009), 939-948 pgs.
Prud'Homme, "Plasmid-based gene therapy of diabetes mellitus", Gene Therapy, (2007), 553-564.
Sciambi, Adam, "Generating Electric Fields in PDMS Microfluidic Devices With Salt Water Electrodes", (Mar. 17, 2014), 5 pgs.
Valero, A, "Gene transfer and protein dynamics in stem cells using single cell electroporation in a microfluidic device", Lab on a Chip 8, (2008), 62-67.
Wang, J., "Vortex-assisted DNA delivery", Lab on a Chip 10, (2010), 2057-2061.
"International Application Serial No. PCT/US2016/027581, International Search Report dated Jul. 26, 2016", 2 pgs.
"International Application Serial No. PCT/US2016/027581, Written Opinion dated Jul. 26, 2016", 5 pgs.

(56) References Cited

OTHER PUBLICATIONS

Dykstra, Peter H., et al., "Microfluidic Electrochemical Sensor Array for Characterizing Protein Interactions with Various Functionalized Surfaces", Anal. Chem., 83(15), (2011), 5920-5927.

Escoffre, Jean-Michael, et al., "What is (Still not) Known of the Mechanism by Which Electroporation Mediates Gene Transfer and Expression in Cells and Tissues", Mol. Biotechnol., 41(3), (2009), 286-295.

Geng, et al., "Microfluidic electroporation for cellular analysis and delivery", Lab Chip vol. 13, (Jul. 8, 2013), 3803-3821.

Mernier, Guillaume, et al., "Continuous-flow electrical lysis device with integrated control by dielectrophoretic cell sorting", Lab on a Chip, 10(16), (2010), 2077-2082.

Persat, Alexandre, et al., "Basic principles of electrolyte chemistry for microfluidic electrokinetics. Part II: Coupling between ion mobility, electrolysis, and acid-base equilibria", Lab on Chip, 9(17), (2009), 2454-2469.

Yun, et al., "Sequential multi-molecule delivery using vortex assisted electroporation", Lab Chip 2013, 13, 2764, [Online]. Retrieved from the Internet: <URL:http://pubs.rsc.org/en/content/arflctetanding/2013/ic/c3lc50196e#ldlv>, (Jul. 21, 2013), 2764-2772.

"U.S. Appl. No. 15/406,210, Response Filed Sep. 5, 2018 to Final Office Action dated Jun. 5, 2018", 10 pgs.

"U.S. Appl. No. 15/406,210, Declaration Under 37 C.F.R. 1.132 filed Sep. 5, 2018", 4 pgs.

"U.S. Appl. No. 15/406,210, Advisory Action dated Sep. 19, 2018", 3 pgs.

"U.S. Appl. No. 15/406,210, Response Filed Feb. 14, 2018 to Non Final Office Action dated Nov. 14, 2017", 9 pgs.

"U.S. Appl. No. 14/703,648, Examiner Interview Summary dated Feb. 5, 2018", 3 pgs.

"U.S. Appl. No. 14/703,648, Non-Final Office Action dated Mar. 1, 2018", 20 pgs.

"U.S. Appl. No. 15/406,210, Examiner Interview Summary dated Feb. 10. 2020", 3 pgs.

"U.S. Appl. No. 15/406,210, Non-Final Office Action dated Sep. 30, 2019", 26 pgs.

"U.S. Appl. No. 15/768,226, Non-Final Office Action dated Dec. 10, 2019", 12 pgs.

"U.S. Appl. No. 15/768,226, Response filed Aug. 21, 2019 to Restriction Requirement dated Jun. 27, 2019", 8 pgs.

"U.S. Appl. No. 15/768,226, Restriction Requirement dated Jun. 27, 2019", 9 pgs.

"U.S. Appl. No. 15/768,226, Preliminary Amendment filed Apr. 13, 2018", 7 pgs.

"Chinese Application Serial No. 201480052982.7, Office Action dated Apr. 1, 2019", (w/ English Translation), 12 pgs.

"International Application Serial No. PCT/US2016/057117, International Preliminary Report on Patentability dated Apr. 26, 2018", 9 pgs.

"International Application Serial No. PCT/US2016/057117, International Search Report dated Jan. 24, 2017", 4 pgs.

"International Application Serial No. PCT/US2016/057117, Written Opinion dated Jan. 24, 2017", 8 pgs.

Ferraldeschi, R., et al., "CK- and small nuclear size circulation tumor cell (CTCs) phenotypes in metastatic castration-resistant prostate cancer (mCRPC)", ASCO University, Abstract No. 209, J Clin Oncol, 32, (Supp.4), (2014), 2 pgs.

Le, T, "In Vitro Propagation and Characterization of Primary Prostate Tumor Stem/Progenitor Cells", UC San Diego Electronic Theses and Dissertations, Retrieved from <https://escholarship.org/content/qt6qh2502q/qt6qh2502q.pdf?t=lq64ro>, (2009), 44 pgs.

Selmeczi, David, et al., "Efficient large volume electroporation of dendritic cells through micrometer scale manipulation of flow in a disposable polymer chip", Biomedical Microdevices, 13(2), (2011), 383-392.

Yun, Hoyoung, et al., "Sequential mufti-molecule delivery using vortex assisted electroporation", Lap Chip, 135(14), (2013), 2764-2772.

"U.S. Appl. No. 15/406,210, Final Office Action dated Jun. 5, 2018", 25 pgs.

"U.S. Appl. No. 15/406,210, Final Office Action dated Jul. 10, 2020", 33 pgs.

"U.S. Appl. No. 15/406,210, Response filed Mar. 30, 2020 to Non Final Office Action dated Sep. 30, 2019", 10 pgs.

"U.S. Appl. No. 15/768,226, Final Office Action dated Jun. 22, 2020", 13 pgs.

"U.S. Appl. No. 15/768,226, Response filed Jun. 10, 2020 to Non Final Office Action dated Dec. 10, 2019", 8 pgs.

Chou, Ting-Chao, "Drug Combination Studies and Their Synergy Quantification Using the Chou-Talalay Method", Cancer Res., 70(2), (2010), 440-446.

Georgiou, et al., "Bleomycin has antiviral properties against drug-resistant HIV strains and sensitises virus to currently used antiviral agents", International Journal of Antimicrobial Agents 27, (2006), 63-68.

\* cited by examiner

US 10,987,670 B2

ELECTRODE ARRAY FOR VORTEX-ASSISTED ELECTROPORATION

RELATED APPLICATION

This application is a U.S. National Stage Filing under 35 U.S.C. 371 from International Application No. PCT/US2016/027581, filed on Apr. 14, 2016, and published as WO 2016/168492, which claims priority to U.S. Provisional Application Ser. No. 62/147,492 (entitled Electrode Array for V 01iexAssisted Electroporation, filed Apr. 14, 2015) both of, which are incorporated herein by reference.

BACKGROUND

Prior vortex-assisted microscale electroporation systems provided limited sample processing throughput.

SUMMARY

A device includes a microfluidic trap disposed along a microfluidic channel, the trap and channel having dimensions to create a fluid vortex within the trap to trap a particle of interest and an electrode having interdigitated electrically isolated fingers positioned in the trap to create an electric field across the trap such that the electric field causes electroporation of a molecule into the particle of interest.

A further device includes an array of microfluidic traps disposed along a set of microfluidic channels, the traps and channels having dimensions to create a fluid vortex within each trap to trap a particle of interest. and an electrode structure having a set of interdigitated electrically isolated fingers positioned in each trap to create an electric field across the trap, and a pair of pads to couple to a voltage source such that the electric field causes electroporation of molecules in the fluid into the particles of interest.

A method includes providing fluid containing particles of interest to an array of traps positioned along multiple channels, the fluid provided at a pressure sufficient to cause vortex flow within the traps and trap one or more particles of interest in the traps and applying a voltage across an electrode structure, the electrode structure having interdigitated electrodes formed in the traps to provide an electric field in the traps to cause electroporation of molecules in the fluid into the trapped particles.

A further method includes forming an electrode array structure on an electrode substrate, the electrode array structure having an array of sets of interdigitated electrically isolated sets of finger electrodes and forming a channel and trap pattern in a device layer over the electrode substrate, such that each trap sealingly covers a corresponding set of interdigitated electrically isolated finger electrodes.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

An optimized electrode geometry for a microfluidic vortex based particle trapping array device facilitates efficient electroporation. In some embodiments, a 4-fold higher throughput (e.g., enhanced parallelization capability) and 10-fold lower operational voltage may be obtained over previous configurations. Some embodiments utilize micropatterned gold electrodes which may be seamlessly integrated with microfabrication process flows, allowing batch productions of the device.

Figure 1:
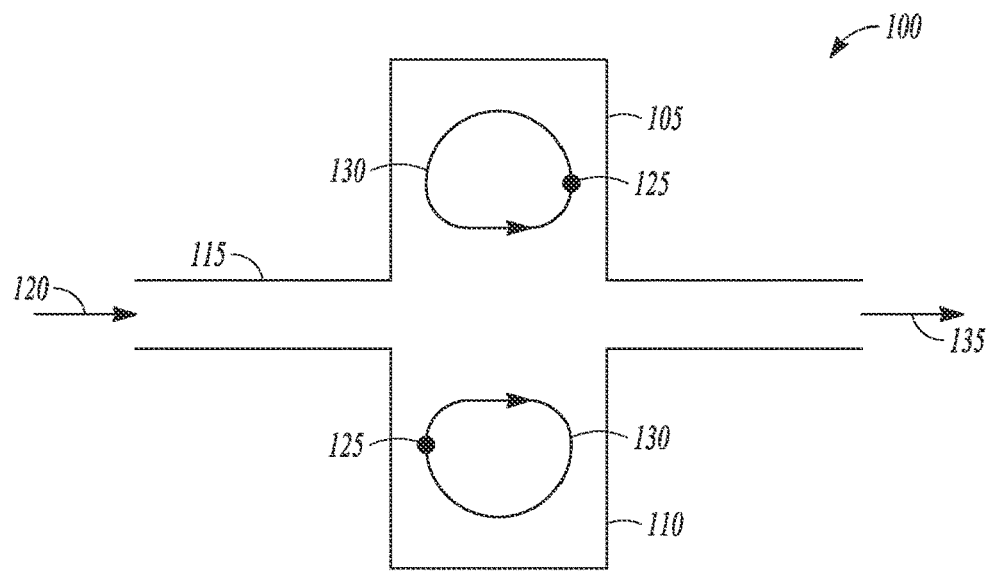
FIG. 1 is a block diagram of an electroporation chamber according to an example embodiment.

FIG. 1 is a simple block diagram of an electroporation device 100. A pair of electroporation traps 105 and 110 are bisected by a channel 115. Together, the traps 105 and 110, along with corresponding portion of the channel 115 form a chamber. Fluid through an input 120 of channel 120 contains particles 125, such as cells, which become trapped in a vortex flow 130 created in each trap 105, 110 when the fluid is flowing through the channel 115 with a Reynolds number of approximately 100. Fluid exits channel 115 via an output 135. Multiple such devices 110 may be assembled in an array consisting of multiple channels and multiple traps per channel. While opposing pairs of traps are shown, forming a chamber that is bisected by the channel, in further embodiments, traps may be formed on only one side of a channel, or alternate on different sides along the length of the channel. Various different geometries of traps may be used from rectangular to semi-circular or other arcuate or geometric shapes suitable for forming a vortex flow and capturing particles. The vortex, and orbit of the vortex may be modified by modifying the geometries and flow rates of the device.

Figure 2:
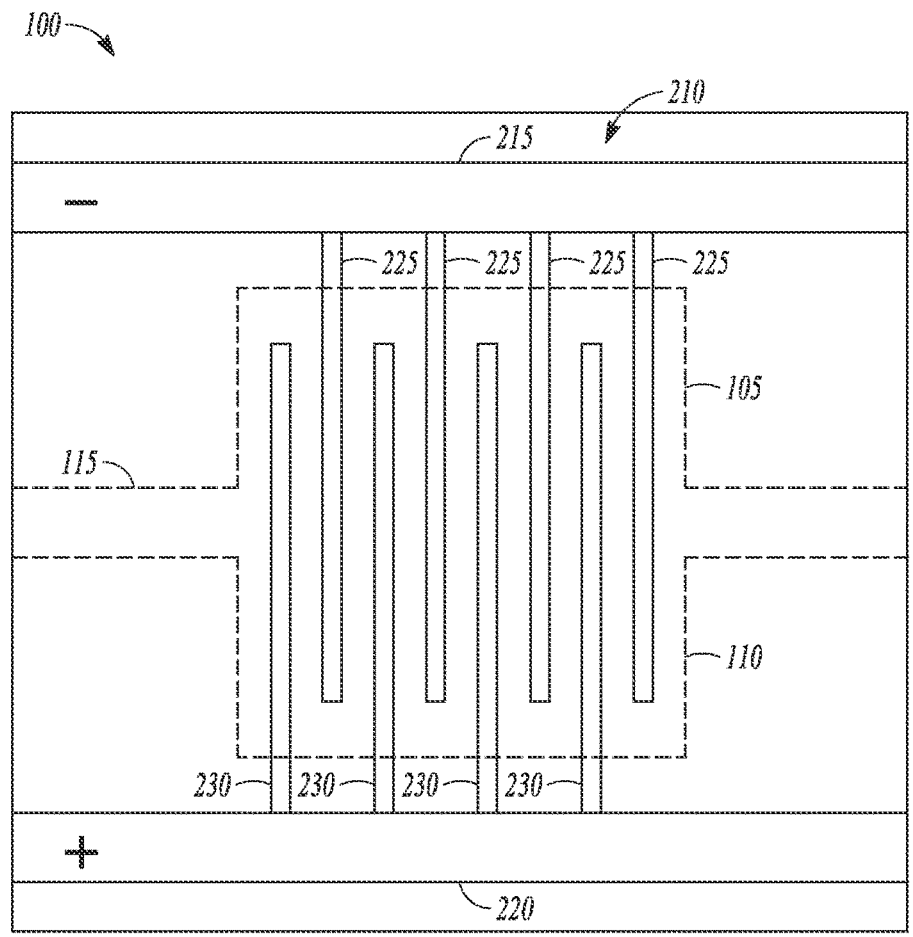
FIG. 2 is a block diagram of the electroporation chamber of FIG. 1 illustrating an interdigitated electrode structure according to an example embodiment.

FIG. 2 is a block diagram of the device 100 in FIG. 1 shown in further detail. The channel 115 and traps 105, 110 are shown as broken lines to facilitate showing a substrate layer having an electrode structure indicated generally at 210. The electrode structure 210 comprises a negative finger connective conductor 215 and a positive finger connective conductor 220 disposed on opposite sides of the traps 105 and 110 respectively. The negative finger connective conductor 215 comprises a plurality of electrode fingers 225 extending from the negative finger connective conductor 215 into the trap 105 and to near the end of trap 110. Similarly, the positive finger connective conductor 220 comprises a plurality of electrode fingers 230 extending from the positive finger connective conductor 220 into the trap 110 and to near the end of trap 105. By only extending to near the end of the respective traps, only one set of electrode fingers need be accounted for when creating a seal between the electrode substrate and a channel and trap layer that are coupled to form the device 100. The respective sets of electrode fingers are interleaved in an alternating manner to create the ability to generate an electric field when a voltage is applied across the connective conductors 215 and 220. Note that the positive and negative connotations of the electrode structure may be reversed in further embodiments.

In some embodiments, the electroporator device 100 is composed of two layers: A glass slide with patterned conductive electrodes (Au for example) on the surface enclosed with a fluidics layer having an array of cell trapping chambers and channels. The fluidics array may be formed of PDMS in one embodiment. Plastic (COP, COC, PMMA, PC) and other suitable materials may also be used. The slide with electrodes may be glass or other material suitable for forming conducting electrodes and mating with the fluidics layer. The electrode dimension, number of electrodes per chamber, and the gap distance between adjacent electrodes may be optimized such that the chamber area influenced by the electric field is maximized, a cell trajectory does not reside at the tip of the electrodes, thereby enhancing the uniformity of the electric field that cells are experiencing, and the electric field should be sufficient enough to electroporate cells without unwanted electrolysis and bubble formation.

In further embodiments, the electrical resistances at each location may be varied to have different electrical field profiles within each chamber. This is useful to help identify an optimum electric field profile to electroporate a given cell type. The device can be tested with varied electrical resistance to find out the optimum condition. The device can then be changed to create a uniform electric field across all chambers to perform the electroporation. For both cases, the electric field in the chamber is uniform across the width or height of the chamber.

In a further embodiment, cross chamber voltage for each electroporation chamber may be modified individually by carefully tweaking the geometry of connecting electrodes and corresponding electric fields can be predicted using COMSOL and SPICE modeling. With a single injection of the given cell population, their responses to selected series of voltage magnitudes could be assessed simultaneously and rapidly. In addition, by setting up different outlets from the channels, cells, from the same batch but treated with different electroporation conditions or chemical doses, can be collected separately for parametric studies.

In still further embodiments, Au electrodes embedded in one or more chambers may serve as sensing electrodes as well as electric potential sources. With appropriate biochemical surface modification corresponding to target analytes, these electrodes, or a further set of electrodes in one or more chambers may be used to pick up minute electrical signal change (typically current) in correlation with the response of trapped cell population to specific chemical/biological stimuli applied in the chamber. The electrical component connected to the device may be modified accordingly to collect and amplify the signal while deducting background noise.

The use of an array may increase the overall throughput per batch and make the electroporation process more efficient and practical. However, simply adding more electroporation units does not guarantee replication of the same performance of the device with a single electroporation unit. The rationales for the optimum layout design of the electroporator array, especially the connecting electrode pattern include: (1) to maximize voltage efficiency of the electroporation array, (i.e., to minimize the voltage drop (waste) outside the cell-trapping chamber area), (2) to precisely predict electric fields being applied to orbiting cells and apply a uniform electric field across all chambers, or apply distinctive electric fields to different chambers to identify optimum conditions for given cells; and (3) to ensure sealing between PDMS and glass substrate. In some embodiments, wider connecting electrodes may be used to minimize the voltage variation across each chamber (trap) while a narrower electrode width is desired to ensure sealing.

Figure 3:
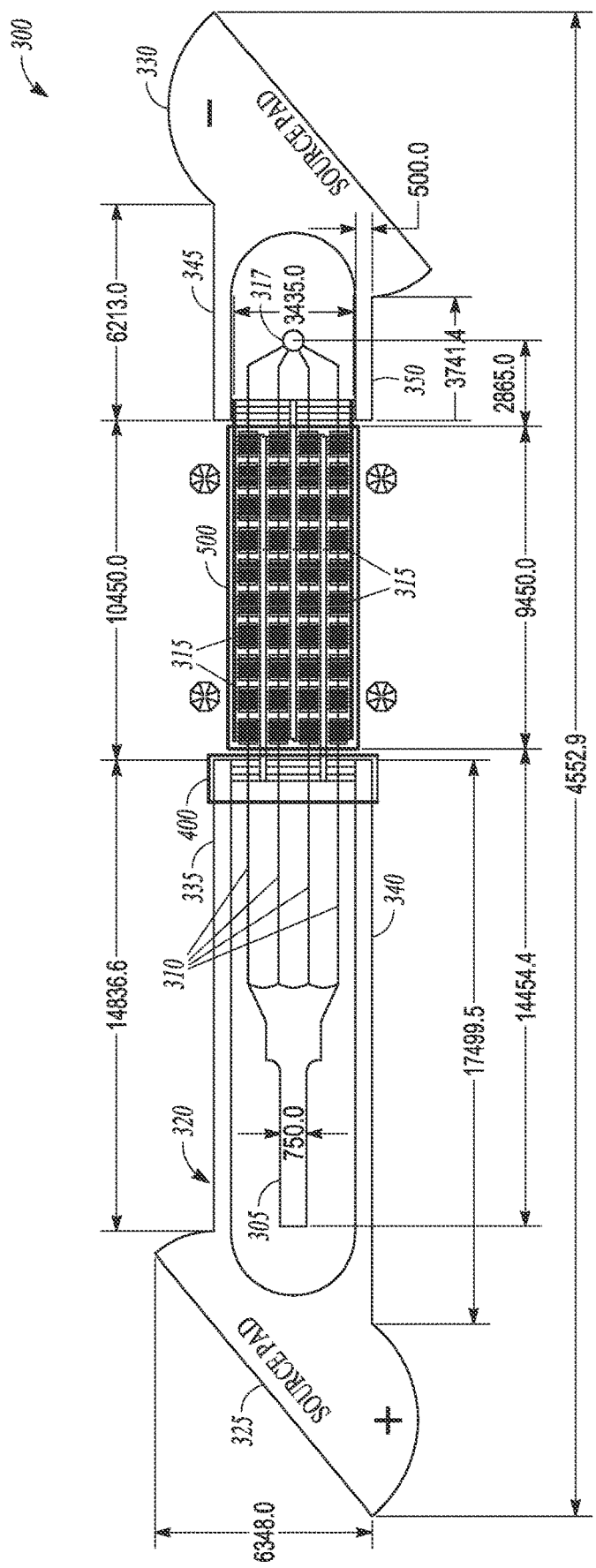
FIG. 3 is a block schematic diagram of an electroporation device including an array of electroporation chambers and channels, with an electrode structure according to an example embodiment.
Figure 4:
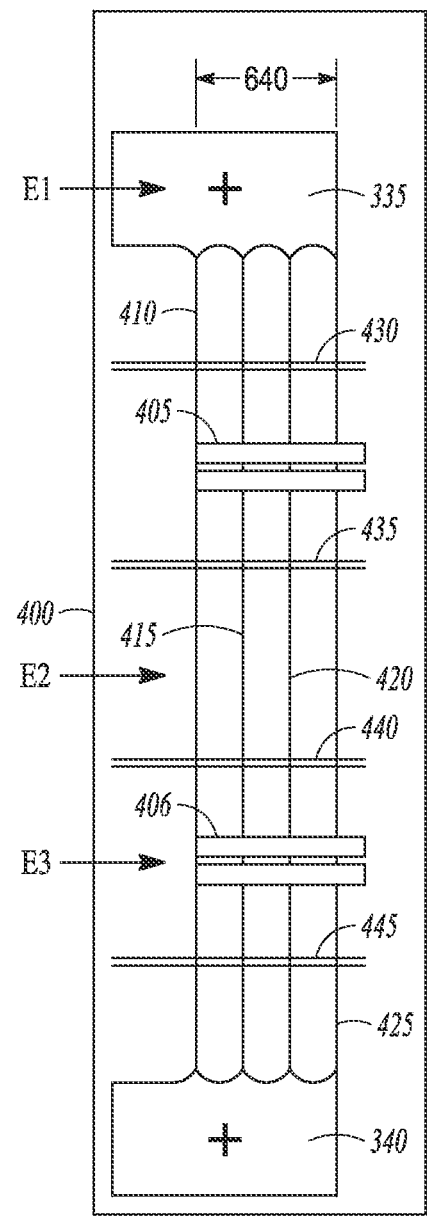
FIG. 4 is a block schematic diagram of cross connectors for an electrode structure according to an example embodiment.
Figure 5:
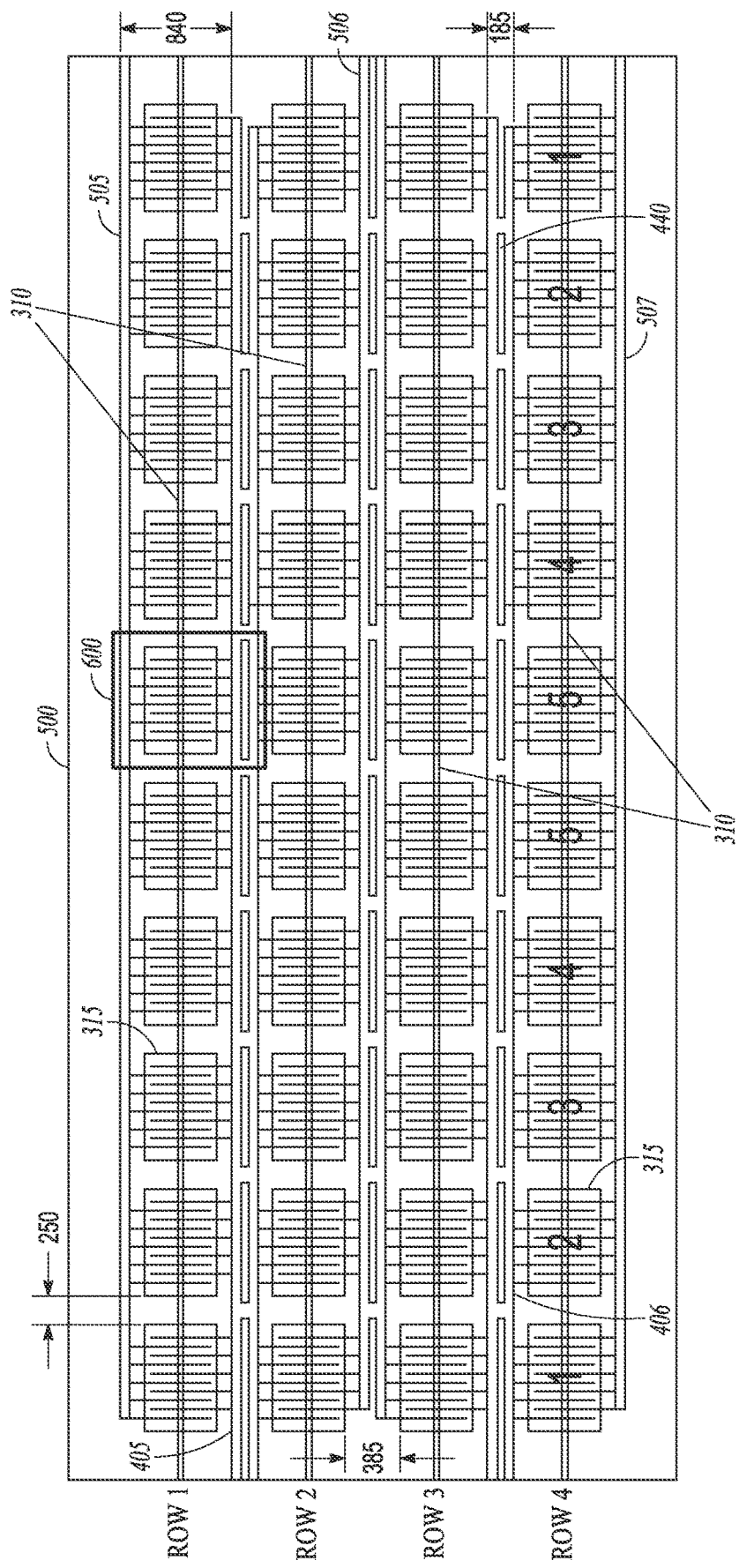
FIG. 5 is a block schematic diagram of an array of electroporation chambers and corresponding electrode structure according to an example embodiment.
Figure 6:
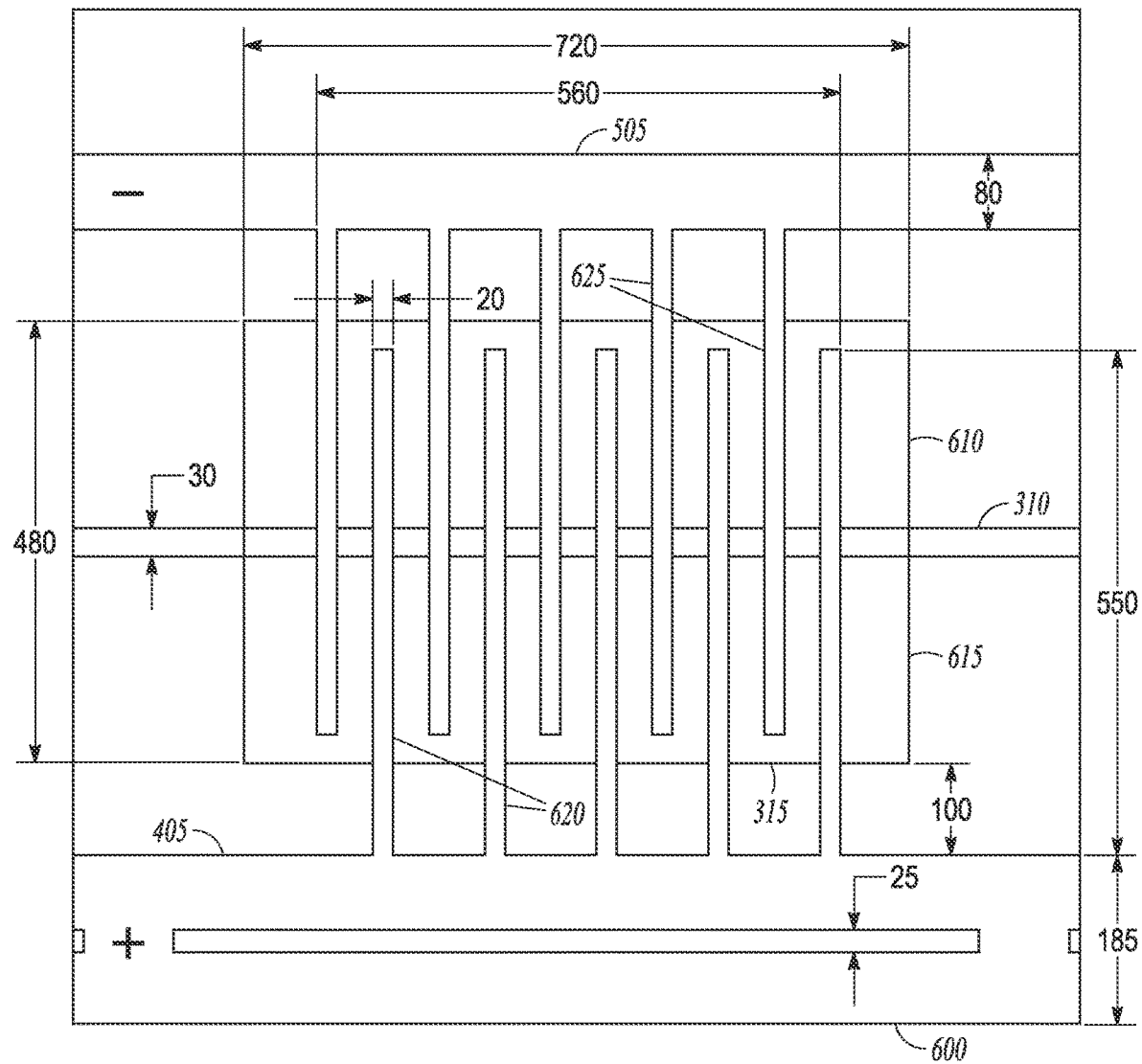
FIG. 6 is a block schematic diagram illustrating interdigitated finger electrodes within a chamber of an array of electroporation chambers according to an example embodiment.

An example microscale electroporator symmetrical array is illustrated in FIG. 3 at 300, with FIGS. 4, 5, and 6 showing further detail of elements of FIG. 3. In one embodiment, the array 300 includes an input fluid channel 305 that branches into four chamber channels 310 that each contains 10 chambers 315. The channels 310 proceed through the array of chambers and empty at 317. Each chamber comprises a pair of opposed traps extending from the chamber channels 310, as shown in further detail in FIG. 6. The array thus includes 40 chambers (4 rows×10 chambers per each row, i.e., a total of 80 cell trapping vortices per device at its full capacity). In one embodiment, sets of four neighboring chambers (2×2) are positioned such that they can be fit into a single field of view of a camera (not shown) when a 4× objective is used. 10 multi-point automated imaging sequences may be used to visualize and monitor all 80 cell-trapping vortices in real time during electroporation. In further embodiments, other sensing mechanisms may also be employed.

An electrode structure is illustrated generally at 320 and is formed of various widths of conductors, which may also be referred to as conductors or connecting wires. A source pad 325 provides a convenient conductive pad for coupling to a positive voltage source, and a source pad 330 provides for coupling to a negative voltage source. The sources may be reversed in one embodiment, and may be variable voltage or DC voltage sources. Variable voltages include square wave sources and AC sources to name a few. The electrode structure 320 also includes two connective conductors indicated at 335 and 340 to couple to further finger connective conductors shown in further detail with interdigitated finger conductors in FIG. 5. Similarly, the negative source pad 330 branches into two connective conductors indicated at 345 and 350, which further branch into finger connective conductors and interdigitated finger conductors, forming the array of finger conductors to create a desired electric field in the traps for electroporation.

Sets of cross conductors is illustrated at 400, and serve to couple the finger connective conductors, indicated at 405 and 406 to each other, providing a failsafe for broken conductors and further enhancing the voltage uniformity of the electrodes in each trap. As seen in FIG. 4 at 400, there are four cross conductors 410, 415, 420, and 425 and addition orthogonal cross conductors 430, 435, 440, and 445 coupled to the connective conductors 335 and 340. Similar cross conductors may be used for connective conductors 345 and 350 as shown in FIG. 3.

The two finger connective conductors 405 and 406 are sufficient to couple to positive interdigitated finger conductors in each of the chambers. Conductor 405 extends between the first two rows of chambers, and conductor 406 extends between the last two rows of chambers. The finger connective conductors coupled to the negative source pad 330 branch into three, extending along the outsides of the first and fourth rows of chambers and between the second and third rows of chambers. In one embodiment, the finger connective conductors extending between rows may comprise a conductor for each row, which may be periodically interconnected along their length.

Within each PDMS cell trapping chamber ($L_c$=720 µm; $W_c$=480 µm; $H_c$=70 µm), there are 5 pairs of interdigitated Au electrodes (20 µm×450 µm) in one embodiment. For each row, electrodes with the same polarity are connected with a single wire (denoted as E3 corresponding to 405 and 406, $W_{E3}$=80 µm), transferring electric signals from the source. Several connecting points may be formed between two adjacent wires to eliminate chances of device malfunctions due to fabrication defects. The connecting wires were designed to have two sections of varied electrode widths. The first section (denoted as E1 corresponding to 335 and 340), which is immediately after the electric source pad 325, are designed to have electrode length and width of $L_{E1}$≈16 mm and $W_{E1}$=500 µm, respectively. The first section electrodes are then branched into the second sets of 4 connecting electrodes 410, 415, 420, 425, denoted as E2, whose length and width are $L_{E2}$≈3 mm and $W_{E2}$=20 µm. The first and second sections of electrodes are located orthogonally in order to deliver electric signals to each row of the electroporation chambers. The purpose of four repeating E2 cross connectors may be to lower the overall electrical resistance across those electrodes (i.e., lowering the voltage loss) by parallelizing resistors while eliminating the leakage of injected fluids at the site where Au electrodes are in contact with PDMS. The number and widths of the repeating connectors can be varied in order to intentionally vary electric fields for each chamber. The width of the electrodes, directly under the edge of electroporation chamber (where PDMS and glass substrate are bonded) should be smaller than 20 um for a 300 nm thick Au layer. Otherwise, the injected fluid may leak between the chamber and substrate where the connectors traverse the substrate under the edge of the chamber. In one embodiment, the value of $W_{E2}$=20 µm is small enough to help ensure sealing, such as irreversible sealing, between a substrate layer on which the electrodes are formed and a device layer in which the traps and channels are formed. In one embodiment, the electrodes may be formed on a glass slide with micropatterned 300 nm-thick Au electrodes and the traps and channels may be formed in a PDMS layer. These values are just examples, and may be varied in further embodiments.

FIG. 5 provides a larger view of the array at 500. Note that the reference numbers used in FIGS. 3, 4, 5, and 6 are consistent. The finger connective conductors 405 and 406 are illustrated running between the rows from positive source pad 325. Further finger connective conductors 505, 506, and 507 are shown running outside of the outer rows (505 and 507) and between (506) the second and third rows from the negative source pad 330. A chamber area identified by a box 600 is shown in further detail in FIG. 6.

Chamber area 600 shows the chamber 315 and channel 310 bisecting a pair of traps 610 and 615. Positive finger connective conductor 405 is shown at one side of chamber 315, with negative finger connective conductor 505 shown at an opposite side of chamber 315. Note that the finger connective conductors are shown running in substantially the same direction as the channels, and are located outside the boundaries of the chamber.

Positive finger electrodes 620 run from the positive finger connective conductor 405 toward the negative finger connective conductor 505, and negative finger electrodes 625 run from the negative finger connective conductor 505 toward the positive finger connective conductor 405. Both sets of finger connective conductors in one embodiment interdigitate and extend to almost a far end of the chamber, without going further than the chamber wall to ensure a better seal of the chamber to the electrode substrate. In one embodiment, there are five each of the positive finger conductors and negative finger conductors interleaved to form a uniform electric field distribution over the area of the chamber corresponding to the electrode substrate. The field strength weakens as the distance in the chamber orthogonal to the electrodes increases.

Square waves may show slightly better performance compared to that of sine wave in terms of electroporation efficiency when the identical peak AC voltage is applied. The effectiveness may be related to the root mean square (i.e., $V_{rms}$) of the voltage, rather than the absolute magnitude, $V_{pk}$, for electroporation.

Due to the minute gap between the two adjacent electrodes (40 µm), the correct frequency choice should be made for the proper functioning of the electroporator array. Note that adjacent electrodes of opposite polarity are electrically isolated from each other except for any conductivity provided by the fluid.

If the frequency is too low (f<10 kHz, the lower limit of the feasible frequency range for the current configuration), bubbles may be generated inside the electroporation chambers. Bubble generation may interfere with cell trapping stability and may also damage the Au electrodes. On the other hand, if the frequency is too high, such as f>40 kHz in one embodiment, the rapid shift of electric field polarization may diminish the electroporation process. In one embodiment, 20 kHz was chosen as the optimal frequency for the current electroporator array with cells of interest.

Various pulse numbers were tested to evaluate whether extra pulses would lead to dramatic performance enhancement. Both the electroporation efficiency and cell viability were similar when either 6 or 10 pulses were applied, especially at higher voltage (i.e., >12 $V_{pk}$), suggesting that within the tested voltage range, using 10 pulses will not cause adverse effects to some cells.

Based on the discussion above, the standard parameters used for some experiments to perform electroporation were set to be a square wave with 20 kHz, 10 pulses, 1 ms pulse width and 1 s interval between each pulses unless otherwise specified. Adopting the standard parameter, electroporation at different voltage levels were conducted and cells were collected downstream into 96 well plates after electroporation for evaluation. Further analysis revealed $V_{pk}$=14.5 V as an optimal voltage for HEK 293. It was also noticed that the total cell number collected in the well plate dropped dramatically at relatively higher voltage ranges (>17 $V_{pk}$). Presumably, it is due to either the interference of bubble generated inside the chamber or trapped cell bursting occurred at high voltage. Therefore, when 17<$V_{pk}$, the electroporator array suffers from low number of collected cells although the efficiency and viability percentage are still comparable to that of the optimal voltage.

In further embodiments, the voltage may be selected to intentionally lyse or burst selective cells. Different pulse parameters may also be selected. Such a process may be used to create more pure subpopulations of cells to collect downstream.

After target cells are trapped in vortices, various voltages can be applied to trapped cells. Voltages higher than the transmembrane potential of cells would cause irreversible cellular membrane damage to achieve "controlled" cell lysis. Here, the applied voltage can be lower than the voltage inducing electrolysis (i.e., to avoid severe bubble issue). Gradual increase in voltages would enable sequential cell lysis. The intracellular components from burst cells may also be sequentially sampled downstream at each cell-lysis event for further concentration and analysis.

One of the parameters for the performance evaluation of electroporation is the apparent electric field intensity that cells are exposed to. The conventional approach for electric field estimations is to divide the applied voltage magnitude by the distance of two vertical electrodes between which cell solutions reside. However, with the use of planar electrodes located at the bottom of the chamber, the electric field distribution may vary widely across the cell solution over the depth of the chamber. In addition to consequences caused by the planar electrode configurations, the fact that cells are moving in suspension during electroporations suggests that the simple average estimation may not be accurate or reliable. Simulations using COMSOL provide a better understanding of the electric field distribution inside the chamber, particularly at different heights of the chamber and along the cell trajectory. Based on some simulation results, the resistance of single chamber filled with DPBS, whose electrical conductivity is 1.4 S/m, during electroporation was estimated at about 430 Ohm.

During electroporation, both the Au patterns and the conducting solution injected in the microchannel function together as a complex circuit composed of various electrical resistors. The applied voltage reading from the power supply does not necessarily represent the actual voltage across each chamber due to the complexity of the device layout. The use of SPICE simulations prior to electrode manufacturing may be used for verification of circuit/device operation at the transistor level, and may provide guidance for design optimization of devices having varying array and channel sizes and layout.

Figure 7:
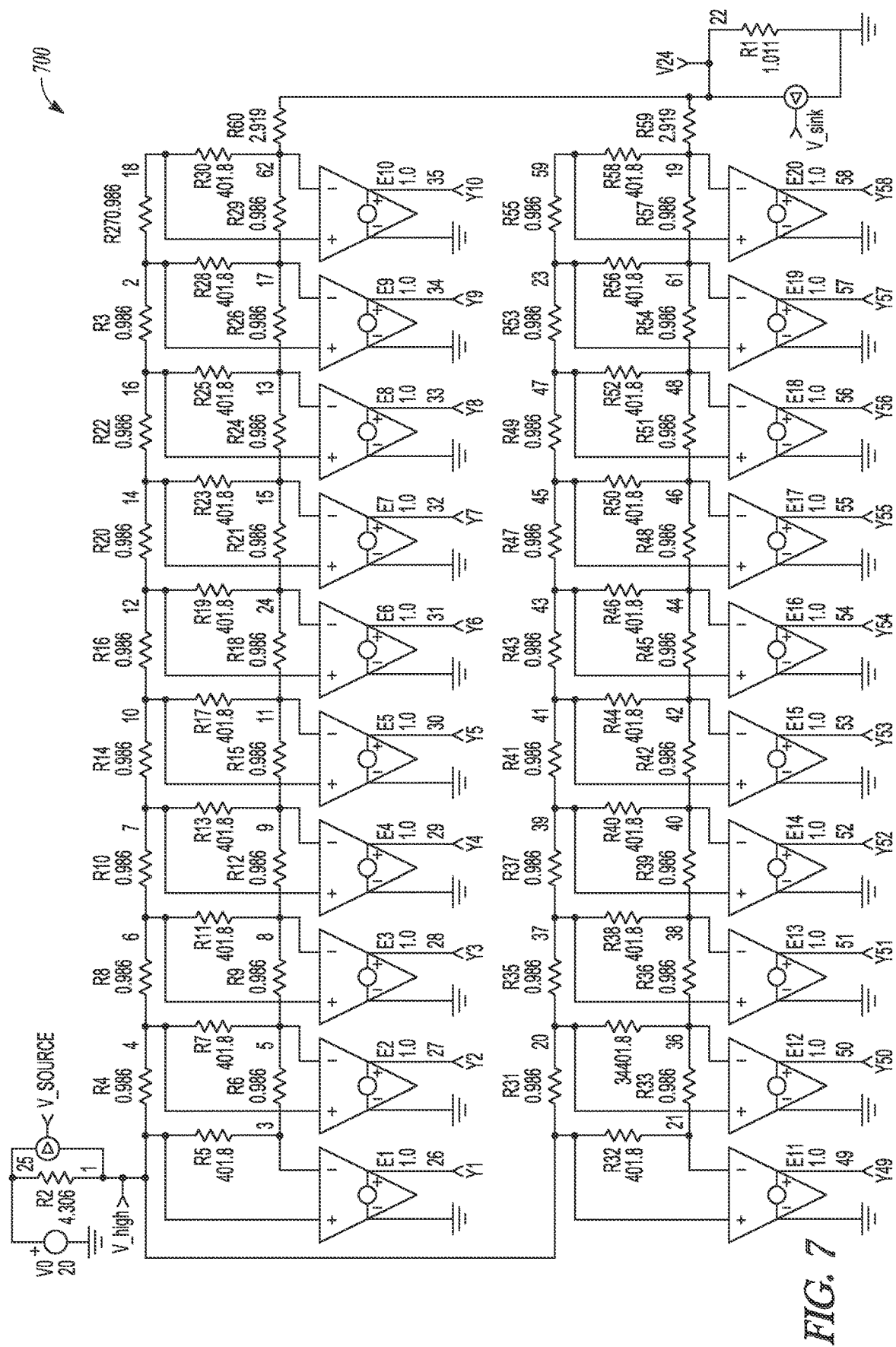
FIG. 7 is a block schematic diagram of a SPICE model for an electroporation array according to an example embodiment.
Figure 8:
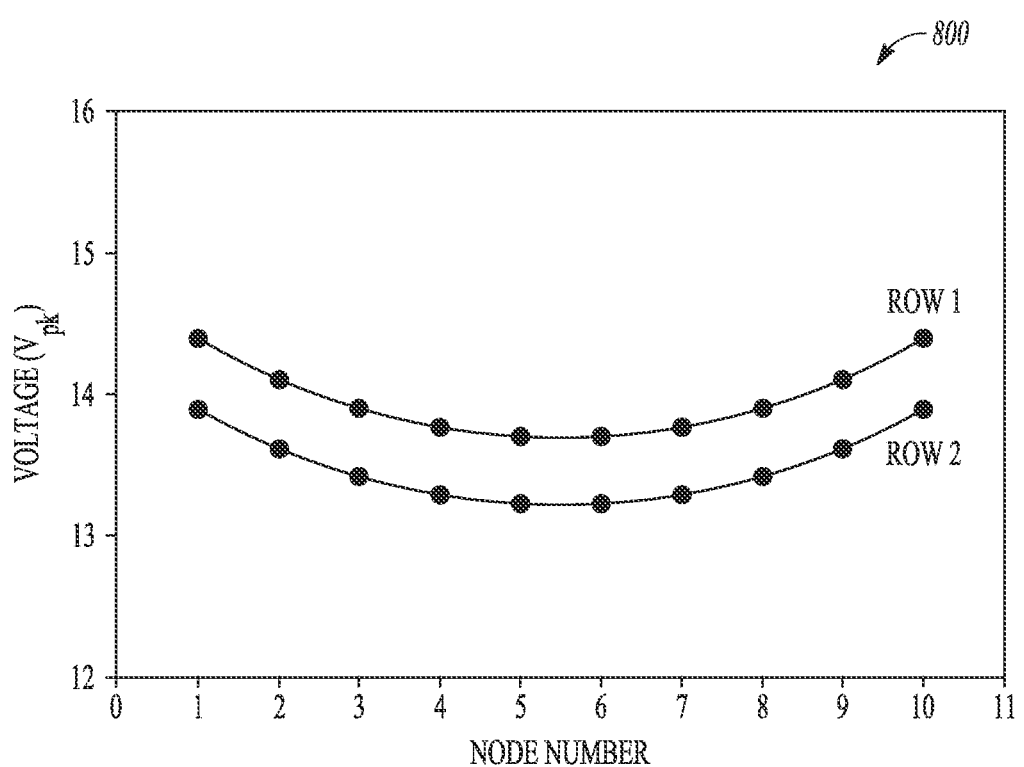
FIG. 8 is a graph illustrating simulated voltage at multiple nodes of an electroporation array according to an example embodiment.

FIG. 7 illustrates a SPICE model 700 of an upper half of the array 500. The lower half of the array shares exactly the same structure. Varying the widths of the different connecting wires results in different resistances, which may be taken into account by the SPICE model. Using the SPICE model 700, cross chamber voltage variation of the first two rows of the array with an input peak voltage, Vpk, of 20 volts is illustrated in a graph 800 in FIG. 8 showing the voltage at each node. Each circle or node on the graph corresponds to a chamber. The same model may be used to design an electrode array with intentionally varied resistances at each chamber in further embodiments. Such embodiments may be useful in identifying and confirming electrode arrays to obtain desired performance in different situations, such as for electroporating, lysing, or sensing different particles or cells.

Criteria which may be used to assess the electroporator array performance include: (1) chamber voltage efficiency, which refers to how much fraction of applied voltage actually available at the cell trapping chambers for sufficient electroporation (i.e., part of the applied voltage would be inevitably lost via the connecting Au patterns; (2) Cross chamber voltage variation, which represents that, within the chamber array, how variable the voltages are among individual chambers. Using row 4 in FIG. 5 as an example, chambers 1 to 5 have different cross chamber voltages due to the variation in lengths of the finger connective conductors. Typically the more chambers serially connected in one row and/or the more rows one device consists of in parallel, the larger the chamber-to-chamber voltage variation tends to get. For optimization, it is desired to optimize electroporation effectiveness with minimal voltage, and to have uniform electroporation effectiveness across all the chambers on the same device. Based on the calculation using a SPICE model, the balance between the two parameters may be achieved with 80% voltage efficiency and a chamber voltage variation less than 8% for 40 chambers (trap pairs) per device using the dimensions shown. The particular dimensions utilized for the electrode structure and channel and trap sizes may be varied significantly in further embodiments. More or fewer channels and traps per channel may be used. The electrode structure and layout may also be modified. The dimensions, such as length (straight vs. serpentine), width, and number of parallel arrays of electrodes can be modified to create desired electric field profiles within the electroporation chambers. Serpentine geometry may be useful for applications benefiting from higher electrical resistances (Joule heating or large voltage drop across electrodes). The materials used for the electrodes may also be varied, with Au being one material that may be incorporated with other materials, or other conductive materials or combinations of materials may be used, such as platinum, copper, and aluminum for example.

Due to the "independent", yet "flexible", nature of the device having a wide range of modifiable parameters (e.g., chamber geometry, chamber height, fluid conductivity, electrode geometry and electric field distribution), the device may serve as a fine model to combine with theoretical studies such as electrolysis and electroporation mechanism to provide experimental observation as well as validation with an aid of visualization equipment (e.g., high speed camera) and imaging analysis tools (e.g., computer vision algorithms).

In still further embodiments, the electrode array may be used to conduct fundamental studies on electrolysis and determine the thickness of electrical double layer of given conductive solution. This can be very useful tool for designing better next-generation electrical biosensors, and electroporator and/or cell lysis devices.

Examples

1. A device comprising:
a microfluidic trap disposed along a microfluidic channel, the trap and channel having dimensions to create a fluid vortex within the trap to trap a particle of interest; and
an electrode having interdigitated electrically isolated fingers positioned in the trap to create an electric field across the trap such that the electric field causes electroporation of a molecule into the particle of interest.

2. The device of example 1 wherein the electrode is formed on a plane of a first substrate and is enclosed with a first layer having the channel and trap formed therein.

3. The device of example 2 wherein the interdigitated electrically isolated fingers are interdigitated within the trap.

4. The device of any of examples 2-3 wherein the trap comprises a pair of traps opposed from the channel and wherein the electrode comprises:
a first finger connective conductor running in the same direction as the channel and disposed outside one side of the pair of traps;

a second finger connective conductor running in the same direction as the channel and disposed outside the other side of the pair of traps; and wherein the fingers run from each finger connective conductor toward the other finger connective conductor to form an interdigitated array of electrodes.

5. The device of any of examples 2-4 wherein the first substrate comprises glass or plastic, the electrodes comprise gold, and the first layer comprises PDMS or plastic.

6. The device of any of examples 1-5 wherein the device comprises an array of channels, each having a plurality of traps and electrodes.

7. The device of any of examples 5-6 wherein the electrodes include conductive pads and connective conductors coupled to the interdigitated fingers, the conductive pads to couple to plus and minus terminals of a voltage source.

8. The device of example 7 wherein the electrodes are patterned to minimize voltage variations between traps.

9. The device of example 8 wherein the electrode pads are wider than the connective conductors, and wherein the electrodes further comprise:

multiple cross conductors to couple the connective conductors together; and a plurality of finger connective conductors coupled between the connective conductors and sets of the interdigitated fingers, wherein the connective conductors are wider than the finger connective conductors to minimize voltage variation across chambers.

10. The device of example 9 wherein the electrode pads, connective conductors, and finger connective conductors are disposed outside each trap.

11. The device of any of examples 9-10 wherein the trap comprises a pair of traps opposed from the channel and wherein:

each channel has a first finger connective conductor running in the same direction as the channel and disposed outside one side of the pair of traps;

each channel has a second finger connective conductor running in the same direction as the channel and disposed outside the other side of the pair of traps; and wherein the fingers run from each finger connective conductor toward the other finger connective conductor to form an interdigitated array of electrode fingers in each pair of traps.

12. The device of any of examples 6-11 wherein each channel comprises up to 20 traps.

13. The device of any of examples 1-12 wherein the electrode comprises patterned gold.

14. A device comprising:

an array of microfluidic traps disposed along a set of microfluidic channels, the traps and channels having dimensions to create a fluid vortex within each trap to trap a particle of interest; and an electrode structure having a set of interdigitated electrically isolated fingers positioned in each trap to create an electric field across the trap, and a pair of pads to couple to a voltage source such that the electric field causes electroporation of molecules in the fluid into the particles of interest.

15. The device of example 14 and further comprising an input coupled to the set of microfluidic channels for providing fluids containing the particles of interest and selected molecules, and an output to remove fluid from the channels.

16. The device of any of examples any of examples 14-15 wherein the electrodes include finger connective conductors coupled to the interdigitated fingers, wherein the electrode pads are wider than the connective conductors, and wherein the electrodes further comprise:

multiple cross conductors to couple the connective conductors together; and a plurality of finger connective conductors coupled between the connective conductors and sets of the interdigitated fingers, wherein the connective conductors are wider than the finger connective conductors to minimize voltage variation across chambers.

17. A method comprising:

providing fluid containing particles of interest to an array of traps positioned along multiple channels, the fluid provided at a pressure sufficient to cause vortex flow within the traps and trap one or more particles of interest in the traps; and applying a voltage across an electrode structure, the electrode structure having interdigitated electrodes formed in the traps to provide an electric field in the traps to cause electroporation of molecules in the fluid into the trapped particles.

18. The method of example 17 wherein the electrode structure is formed with different connection widths.

19. The method of any of examples 17-18 wherein electrode dimensions are selected to promote variations in electric field profiles in different chambers to identify electrode dimensions that produce a desired electric field profile.

20. The method of example 19 wherein the desired electric field profile is suitable for optimum electroporation or cell lysis.

21. A method comprising:

forming an electrode array structure on an electrode substrate, the electrode array structure having an array of sets of interdigitated electrically isolated sets of finger electrodes; and forming a channel and trap pattern in a device layer over the electrode substrate, such that each trap sealingly covers a corresponding set of interdigitated electrically isolated finger electrodes.

22. The method of example 21 wherein the electrode array structure comprises finger connective conductors running in the same direction as the channels and positioned outside an area enclosed by the traps.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A device comprising:

An array of microfluidic traps disposed along a set of microfluidic channels, the traps and channels having dimensions to create a fluid vortex within the traps to trap particles of interest; and an electrode having sets of interdigitated electrically isolated fingers positioned in the traps to create an electric field across the traps such that the electric field causes electroporation of a molecules into the particle of interest wherein the electrodes include:

a positive conductive pad and a negative conductive pad disposed on opposite sides of the microfluidic channels;

a positive connective conductor and a negative connective conductor coupled the respective conductive pads;

sets of positive and negative finger connective conductors coupled to the interdigitated fingers, and;

sets of cross conductors disposed on opposite sides of the microfluidic channels to couple the positive connective conductor and positive finger connective conductors together and the negative connective conductor and negative finger connective conductors together, wherein the connective conductors are wider than the finger connective conductors and operate with the sets of cross conductors to minimize voltage variation across the traps.

2. The device of claim 1 wherein the electrode is formed on a plane of a first substrate and is enclosed with a first layer having the channels and traps formed therein.

3. The device of claim 2 wherein the interdigitated electrically isolated fingers are interdigitated within the traps.

4. The device of claim 2 wherein the traps comprises pairs of traps opposed from the channels and wherein the finger connective conductors run in the same direction as the channels and are disposed outside one side of the pair of traps and wherein the fingers run from each finger connective conductor toward another finger connective conductor to form an interdigitated array of electrodes.

5. The device of claim 2 wherein the first substrate comprises glass or plastic, the electrodes comprise gold, and the first layer comprises PDMS or plastic.

6. The device of claim 1 wherein the electrode pads, connective conductors, and finger connective conductors are disposed outside each trap.

7. The device of claim 1 wherein each channel comprises up to 20 traps.

8. The device of claim 1 wherein the electrode comprises patterned gold.

* * * * *